(12) United States Patent
Flachsmann et al.

(10) Patent No.: US 7,846,887 B2
(45) Date of Patent: Dec. 7, 2010

(54) CYSTEINE DERIVATIVES WHICH COUNTERACT MALODOUR

(75) Inventors: Felix Flachsmann, Duebendorf (CH);
Markus Gautschi, Fällanden (CH);
Thomas McGee, Chittering (AU);
Richard P. Sgaramella, Hoboken, NJ (US)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 12/665,122

(22) PCT Filed: Jun. 18, 2008

(86) PCT No.: PCT/CH2008/000277

§ 371 (c)(1),
(2), (4) Date: Jan. 13, 2010

(87) PCT Pub. No.: WO2008/154765

PCT Pub. Date: Dec. 24, 2008

(65) Prior Publication Data

US 2010/0179088 A1 Jul. 15, 2010

(30) Foreign Application Priority Data

Jun. 19, 2007 (EP) .................... 07011923

(51) Int. Cl.
*C11D 7/26* (2006.01)
*C11D 7/32* (2006.01)
*C11D 7/34* (2006.01)

(52) U.S. Cl. .............. 510/107; 510/276; 510/492; 510/499; 510/505; 435/113; 564/1

(58) Field of Classification Search .............. 510/107, 510/276, 492, 499, 505; 435/113; 564/1
See application file for complete search history.

(56) References Cited

U.S. PATENT DOCUMENTS

2006/0251597 A1* 11/2006 Yu et al. ............... 424/65

FOREIGN PATENT DOCUMENTS

WO 0135768 A 5/2001

OTHER PUBLICATIONS

XP002472371, C. Starkenmann, "Analysis of a Model Reaction System Containing Cystein and (E)-2-methyl-2-butenal, (E)-2-hexenal or Mesityl Oxide" Journal of Agricultural and Food Chemistry, vol. 51, No. 24, Oct. 18, 2003, pp. 7146-7155.
XP002472634, E.M. Stocking et al., "Total Synthesis of VM55599. Utilization of an Intramolecular Diels-Alder Cycloaddition of Potential Biogenetic Relevance" Journal of the American Chemical Society, vol. 122, No. 8, Mar. 1, 2000, pp. 1675-1683.

* cited by examiner

*Primary Examiner*—Gregory R Del Cotto
(74) *Attorney, Agent, or Firm*—Norris McLaughlin & Marcus, PA

(57) ABSTRACT

Cysteine derivatives of formula (I)

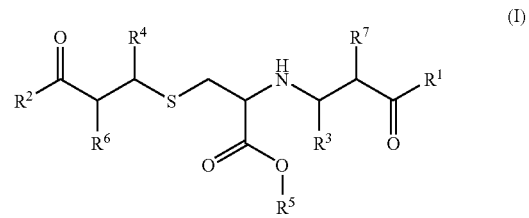

wherein R1-R7 are as defined in the description, and their use as malodor counteractant. Furthermore, a process of their production and consumer products comprising them are described.

8 Claims, No Drawings

CYSTEINE DERIVATIVES WHICH COUNTERACT MALODOUR

This is an application filed under 35 USC 371 of PCT/CH2008/000277.

The present invention refers to 4-aza-7-thiadeca-1,10-dione derivatives having malodor counteracting properties and to consumer products comprising them.

In many parts of the world, there is strong pressure to move to more biodegradable ingredients in consumer products. Unfortunately, these biodegradable ingredients are intrinsically unstable and able to be broken down by bacteria. Some breakdown can occur to a small extent already in the consumer product to which they are added liberating malodorous moieties that make the consumer product smell unpleasant. For example, fabrics, washing liquids and fabric softeners have ingredients that release unpleasant-smelling compounds such as short chain fatty acids, aldehydes and ketones. Thus, additional amounts of perfume may have to be added to a consumer product in order to cover this base odor. Although the perfume may cover the unpleasant odor of the product, frequently these malodorous materials may be deposited on the treated substrate causing it to have a malodor, which may become more evident over time as the co-deposited perfume evaporates. Such malodors are exacerbated at elevated temperature (above about 30° C.) and high humidity (about 50% relative humidity or higher). Furthermore, in some parts of the world, the use of bar soap, derived from relatively cheap animal and vegetable fats, for washing clothing, textiles, skin, hair, cooking utensils, and dishes is commonplace. The effects of the climate and presence of various additives can cause these bars become rancid and thus malodorous. The addition of perfume can musk this to some degree, but not only is this solution not completely effective, but also adds considerably to the cost of the bars. Other consumer products, such as hair colorants, depilatory products, permanent wave products, skin bronzing, skin lightening, or hair removal products, have a strong bad smell because of their active ingredients, which may include for example, ammonia and thioglycolic salts.

Other approaches to reducing malodors are the elimination by absorption of the malodor by a porous or cage-like structure often in combination with aroma chemicals, and avoidance of the formation of malodors by such routes as the addition of antimicrobials and enzyme inhibitors. While these approaches have yielded improvements in malodor control in certain cases this approach is not applicable to consumer products comprising actives possessing strong bad smell. Thus, there still remains a need for further compounds which are more efficient against malodors.

It has now been found that the problem may be substantially or even completely overcome by the addition of a new class of 4-aza-7-thiadecadione derivatives to the consumer product in need thereof.

Thus, the present invention refers in one of its aspects to the use as malodor counteractant of a compound of formula (I)

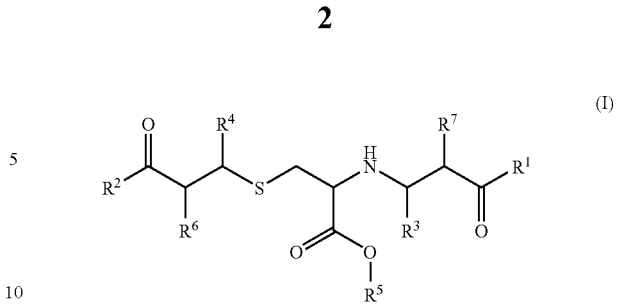

wherein $R^1$ and $R^2$ are independently selected from the group consisting of linear and branched $C_1$-$C_{14}$, e.g. $C_4$-$C_{10}$, alkyl and alkenyl, (e.g. ethyl, 3,4-dimethyl-2-penten-2-yl, 3,4-dimethyl-pent-2-yl, 3,4-dimethyl-2-hexen-2-yl, 3-ethyl-4-methyl-2-hexen-2-yl, 3-ethyl-2-hexen-2-yl, 3,4,4-trimethyl-2-penten-2-yl, but-2-yl, but-3-en-1-yl), cycloalkyl and cycloalkenyl, optionally substituted, comprising 5-14, e.g. 8, 9, 10 or 11, carbon atoms (e.g. 2,6,6-trimethylcyclohex-1-enyl, 2,6,6-trimethylcyclohex-2-enyl, 2,6,6-trimethylcyclohex-3-enyl, 6,6-dimethyl-2-methylenecyclohexyl, 2,6,6-trimethylcyclohex-1,3-dien-1-yl, 2-ethyl-6-methylcyclohex-2-en-1-yl, 2-ethyl-3,6,6-trimethylcyclohex-4-en-1-yl, 2,4,4-trimethylcyclohex-2-en-1-yl, and 2-ethyl-5,5-dimethylcyclopent-2-en-1-yl), and spirobicycloalkyl and spirobicycloalkenyl, optionally substituted, comprising 8-13 carbon atoms (e.g. 7-methylspiro[4.5]dec-6-ene-6-yl, 7-methylspiro[4.5]dec-7-ene-6-yl, 7-methylspiro[4.5]dec-8-ene-6-yl, 7-methylenespiro[4.5]dec-6-yl);

$R^3$ and $R^4$ are independently selected from the group consisting of hydrogen, phenyl, linear and branched $C_1$-$C_6$ alkyl and alkenyl (e.g. methyl, ethyl, isopropyl, hexyl), cycloalkenyl, optionally substituted, comprising 5-12 carbon atoms (e.g. cyclohex-3-en-1-yl), and cycloalkenylalkyl, optionally substituted, comprising 6-14 carbon atoms (e.g. (2,2,3-trimethylcyclopent-3-enyl)methyl);

$R^6$ and $R^7$ are independently selected from hydrogen, linear and branched $C_1$-$C_6$ alkyl and alkenyl (e.g. propyl, methyl, ethyl, hexyl, isopropyl, hexenyl), and cycloalkyl, optionally substituted, comprising 3-14 carbon atoms (e.g. 3,3-dimethylcyclohex-1-enyl, cyclohexyl); or at least one of the pairs $R^1$ and $R^7$, $R^2$ and $R^6$, $R^3$ and $R^7$, $R^4$ and $R^6$ forming together with the carbon atoms to which they are attached a mono- or bicyclic ring system comprising 5 to 10 carbon atoms (e.g. spiro[4.5]decane, 3,3-dimethylcyclohexane, 5,5-dimethylcyclohexane, cyclopentane, cyclohexane, cyclooctane, cycloheptane, cyclohexanone, cyclopentanone); and $R^5$ is selected from the group consisting of linear and branched $C_1$-$C_5$ alkyl (e.g. methyl, ethyl, propyl, iso-propyl, butyl), and $C_7$-$C_{10}$ arylalkyl (e.g. benzyl), optionally substituted with 1, 2, or 3 hetero atoms selected from N, S and O.

As used in relation to compounds of formula (I) unless otherwise indicated "optionally substituted" refers to rings substituted with none, 1, 2, 3 or more substituents selected from $C_1$-$C_3$ alkyl (e.g. methyl, ethyl) or $C_2$-$C_4$ alkenyl (e.g. propenyl, isopropenyl, vinyl, isobutenyl).

The term "malodor counteractant" as used herein refers to a compound according to formula (I) that is capable of interacting with malodor compounds in such a way as to alleviate the offensiveness of the malodor as perceived by the human sense of smell. However it is not intended that this term be limited to any particular mechanism by which such a result may be obtained.

The compounds of formula (I) may be added to a wide variety of consumer products. Thus a further embodiment of the present invention refers to consumer products comprising an effective amount of a compound of formula (I), or mixtures thereof and a consumer product base.

The term "consumer product" as used herein means any composition comprising ingredients that help to solve consumer problems, such as removing dirt and stains, making treated articles softer, treating hair, removing hair, conditioning, lightening and darkening skin, and the like. Examples include, but are not limited to, skin cream and lotions, washing detergents, fabric softener, depilatories, hair dying products, skin bronzing sprays, creams and lotions, shower gels, and soaps of all kinds.

The term "consumer product base" as used herein means a composition for use as a consumer product to fulfill specific actions, such as cleaning, softening, and caring or the like. Examples of such products include fabric care and personal care products such as laundry care detergents, rinse conditioners, personal cleansing compositions. The composition may comprise a variety of active ingredients such as surfactants, polymers, fillers and excipients.

Typically the consumer product comprises from about 0.001% to about 20% by weight of at least one compound of formula (I) as hereinabove defined, based on the end-product. The effective amount of the compound(s) of formula (I) employed in a consumer product base is an amount to provide a malodor counteractant composition that abates a given malodor and it depends on the type of product into which the compound of formula (I) or a mixture thereof is admixed. For example, if used in a soap base the level is from about 0.001% to about 2% by weight of the soap base. If used in a fabric washing liquid the amount is from about 0.01 to 20% by weight of the detergent liquid base. If used in a liquid fabric softener the amount is from about 0.01% to about 10% preferably 0.02 to 5% by weight of the softener liquid base. In general, the amount of a compound of formula (I) present is the ordinary dosage required to obtain the desired result. Such dosages may easily be evaluated by experiments known to the person skilled in the art.

In a further embodiment, the compound according to the present invention may be combined with other ingredients and excipients well known in the art, in particular fragrance ingredients, other malodor counteracting ingredients, and malodor absorbers, or mixtures thereof.

The term "fragrance ingredient" as used herein means any fragrance raw material selected from the extensive range of natural and synthetic molecules, such as extracts, essential oils, absolutes, resinoids, resins, concretes etc., but also synthetic materials such as hydrocarbons, alcohols, aldehydes, ketones, ethers, acids, esters, acetals, ketals, nitrites, etc., including saturated and unsaturated compounds, aliphatic, carboxylic, and heterocyclic compounds. These compounds are known to the person skilled in the art and are described e.g. in Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA. The fragrances may contain organic solvents that are known in the art, such as ethers, straight or branched chain alcohols and diols, volatile silicones, dipropylene glycol, triethyl citrate, ethanol, isopropanol, diethyleneglycol monoethyl ether, diethyl phthalate, triethyl citrate, isopropyl myristate, etc., hydrocarbon solvents such as Isopar™ series by ExxonMobile Chemical Company or the Dowanol series by Dow Chemicals and others, and mixtures thereof.

Optionally, the compounds of formula (I) as hereinabove defined may be combined with other malodor counteracting ingredients, such as benzyl cinnamate, aldehyde C10, heliotropin (3,4-methylenedioxybenzaldehyde), tolyl aldehyde, cinnamic aldehyde, alpha-amyl-cinnamic aldehyde, alpha-hexyl-cinnamic aldehyde, vanillin, benzaldehyde, cuminic aldehyde (4-isopropylbenzaldehyde), anisyl acetate, benzyl salicylate, dihydro eugenol, geraniol, methyl eugenol, para cresyl methyl ether, styrallyl acetate, anisic aldehyde, o-allyl-vanillin, ethyl-aubepin (4-ethoxybenzaldehyde), ethyl-vanillin, carvacrol, 5-methyl-2-(2-methylpropyl)-1,3-dioxane, methyl 1,4 dimethylcyclohexylcarboxylate, iso-Eugenol, Elintaal (acetaldehyde ethyl linalyl acetal), Dispirone (7,9-dimethylspiro[5,5]-undecanone-3), 4-tert-amyl cyclohexane, p-t-butyl-alpha-methyl hydrocinnamic aldehyde, 2-n-heptyl cyclopentanone, alpha cetone (3-methyl-4-(2,6,6-trimethylcyclohex-2-enyl)but-3-en-2-one), beta-methyl naphthyl ketone, cyclohexadecanolide, ethylene brassylate, cyclopentadecanolide, cyclopentadecanone, nonanediol-1,3-diacetate, nonanolide-1,4 (5-pentyldihydrofuran-2(3H)-one), iso-nonyl acetate, nopol acetate (2-(6,6-dimethylbicyclo[3.1.1]hept-2-en-2-yl)ethyl acetate), Dimyrcetol (mixture of 2,6-dimethyloct-7-enol-2 & formate), phenylethyl alcohol, tetrahydro muguol (mixture of 3,7-dimethyloctanol-3 & 2,6-dimethyloctanol-2), 4-tert-butylcyclohexyl acetate, iso-amyl salicylate, clove leaf oil, benzoin siam resinoids, bergamot oil, geranium oil, patchouli oil, petitgrain oil and thyme oil, or mixtures thereof.

In a further embodiment the compounds of formula (I) as hereinabove defined may be combined with malodor absorbers, such as activated charcoal, zeolites, ground corn cob, cyclodextrins and zinc ricinoleate, or mixtures thereof.

In a further embodiment the present invention refers to a method of enhancing the malodor counteractant properties of consumer product, comprising admixing to a consumer product base, e.g. personal care product, household product or cosmetic product, a compound of formula (I) as defined herein above.

The compounds of formula (I) may be added directly to the consumer product base. Alternatively, the compounds of formula (I) may be pre-mixed with other ingredients well known in the art, in particular fragrance ingredients, other malodor counteracting ingredients and malodor absorbers, or mixtures thereof, prior to adding said composition to a consumer product base. In another embodiment the compounds of formula (I) may be added as part of a controlled release system known in the art. Without being limited thereto, such controlled systems include: spray dried particles, agglomerated particles, spray coated particles, enrobed particles, pan-coated particles, hydrogel caps and the like to provide an initial dosage of the malodor counteractant of formula (I), or a mixture thereof.

According to our best knowledge none of the compounds have been described in the literature. Accordingly, the present invention refers in a further aspect to compounds of formula (I)

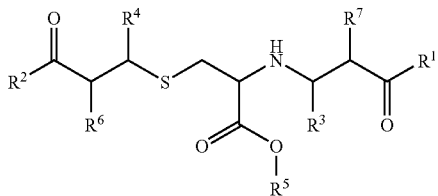

wherein $R^1$ to $R^7$ have the same meaning as given above.

The compounds of the present invention comprise several chiral centres and as such may exist as mixtures of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Non-limiting examples are those compounds of formula (I) wherein $R^1=R^2$, $R^3=R^4$, and $R^6=R^7$.

Further non-limiting examples are those compounds of formula (I) wherein $R^1=R^2$, $R^3=R^4$, $R^6=R^7$, and $R^5$ is methyl, ethyl or benzyl.

Further non-limiting examples are those compounds of formula (I) wherein $R^1$ and $R^2$ are selected from $C_4$, $C_5$, $C_6$ and $C_7$ linear or branched alkenyl, and $R^6$ and $R^7$ are selected from hydrogen, methyl, and benzyl.

Further non-limiting examples are those compounds of formula (I) wherein $R^1$ and $R^2$ are selected from cycloalkyl and cycloalkenyl comprising 8, 9, 10 or 11 carbon atoms, the ring being substituted with 2 or 3 substituents selected from methyl and ethyl, and $R^6$ and $R^7$ are selected from hydrogen, methyl, and benzyl.

Further non-limiting examples are those compounds of formula (I) wherein $R^1$ and $R^2$ are selected from spirobicycloalkenyl comprising 10, 11, or 12 carbon atoms, wherein at least one ring is substituted with at least 1 substituent selected from methyl, ethyl and vinyl, and $R^6$ and $R^7$ are selected from hydrogen, methyl, and benzyl.

Further non-limiting examples are those compounds of formula (I) wherein $R^1$ and $R^2$ are selected from $C_4$, $C_5$, $C_6$ and $C_7$ linear or branched alkenyl and the pairs $R^3$ and $R^7$, and $R^4$ and $R^6$ forming together with the carbon atoms to which they are attached spiro[4.5]decane, 3,3-dimethylcyclohexane, or 5,5-dimethylcyclohexane.

Particularly preferred are compounds of formula (I) selected from the group consisting of methyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate (Example 1), methyl 2-(5,6,7-trimethyl-4-oxooct-5-en-2-ylamino)-3-(5,6,7-trimethyl-4-oxooct-5-en-2-ylthio)propanoate (Example 2), ethyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate (Example 3), ethyl 2-(5,6,7-trimethyl-4-oxooct-5-en-2-ylamino)-3-(5,6,7-trimethyl-4-oxooct-5-en-2-ylthio)propanoate (Example 4), ethyl 2-(4-oxo-4-(2,6,6-trimethylcyclohexa-1,3-dienyl)butan-2-ylamino)-3-(4-oxo-4-(2,6,6-trimethylcyclohexa-1,3-dienyl)butan-2-ylthio)propanoate, ethyl 2-(4-oxo-4-(2,6,6-trimethylcyclohex-2-enyl)butan-2-ylamino)-3-(4-oxo-4-(2,6,6-trimethylcyclohex-2-enyl)butan-2-ylthio)propanoate, ethyl 2-(4-oxo-4-(2,6,6-trimethylcyclohex-1-enyl)butan-2-ylamino)-3-(4-oxo-4-(2,6,6-trimethylcyclohex-1-enyl)butan-2-ylthio)propanoate, ethyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate, ethyl 2-(4-oxo-4-(2,4,4-trimethylcyclohex-2-enyl)butan-2-ylamino)-3-(4-oxo-4-(2,4,4-trimethylcyclohex-2-enyl)butan-2-ylthio)propanoate, ethyl 2-(4-(2-ethyl-3,6,6-trimethylcyclohex-2-enyl)-4-oxobutan-2-ylamino)-3-(4-(2-ethyl-3,6,6-trimethylcyclohex-2-enyl)-4-oxobutan-2-ylthio)propanoate, ethyl 2-(4-(6-ethyl-2-methylcyclohex-3-enyl)-4-oxobutan-2-ylamino)-3-(4-(6-ethyl-2-methylcyclohex-3-enyl)-4-oxobutan-2-ylthio)propanoate, ethyl 2-(4-(3,3-dimethylcyclohex-1-enyl)-4-oxobutan-2-ylamino)-3-(4-(3,3-dimethylcyclohex-1-enyl)-4-oxobutan-2-ylthio)propanoate, ethyl 2-(2-cyclohexyl-3-oxohept-6-enylamino)-3-(2-cyclohexyl-3-oxohept-6-enylthio)propanoate, ethyl 2-(7-hex-5-enoylspiro[4.5]decan-8-ylamino)-3-(7-hex-5-enoylspiro[4.5]decan-8-ylthio)propanoate, ethyl 2-(6-hex-5-enoyl-2,2-dimethylcyclohexylamino)-3-(6-hex-5-enoyl-2,2-dimethylcyclohexylthio)propanoate, ethyl 2-(2-hex-5-enoyl-4,4-dimethylcyclohexylamino)-3-(2-hex-5-enoyl-4,4-dimethylcyclohexylthio)propanoate, and benzyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate.

The reaction of 2-amino-3-mercapto propionic acid (cystein) with substituted 3-buten-2-ones is known to yield only 1,4-S-adducts (C. Starkenmann, *J. Agric. Food Chem.* 2003, 51, 7146). We now surprisingly found that the reaction of 2-amino-3-mercapto propionic acid esters with two equivalents of a suitably substituted 3-buten-2-one results in compounds of the present invention.

The 2-amino-3-mercapto propionic acid esters may be used as the free amine or in the form of an ammonium salt, such as the hydrochloride. In this case, the free base must be liberated in situ by the addition of an organic or inorganic base, such as $K_2CO_3$ or ethyl diisopropyl amine. The reaction may be carried out solventless or in a solvent, such as an alcohol (e.g. methanol or ethanol, preferably the same as present in the starting 2-amino-3-mercapto propanoic acid ester). Alternatively, a high-boiling solvent such as dipropylene glycol may be used which is not removed after reaction. Solvents which are commonly used in perfume compositions, such as isopropylmyristate, and benzyl benzoate, are also preferred. The reaction is conducted at a temperature between 40-100° C., preferably between 50-80° C., and the conversion is followed by analytical means, such as thin layer chromatography, or by instrumental analytics, such as $^1$H-nuclear magnetic resonance spectroscopy.

The products are obtained in sufficiently pure form by filtration to remove salts formed during the reaction and subsequent evaporation to remove solvents. Alternatively, the mixture might be subjected to an aqueous workup, the details of which are known to the person experienced in the art of organic synthesis.

Thus the present invention refers in a further aspect to a method of producing a compound of formula (I)

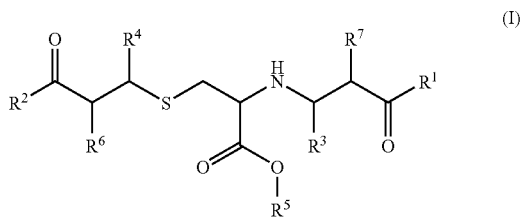

(I)

wherein

R¹ and R² are independently selected from the group consisting of linear and branched $C_1$-$C_{14}$, e.g. $C_4$-$C_{10}$, alkyl and alkenyl (e.g. ethyl, 3,4-dimethyl-2-penten-2-yl, 3,4-dimethyl-pent-2-yl, 3,4-dimethyl-2-hexen-2-yl, 3-ethyl-4-methyl-2-hexen-2-yl, 3-ethyl-2-hexen-2-yl, 3,4,4-trimethyl-2-penten-2-yl, but-2-yl, but-3-en-1-yl), cycloalkyl and cycloalkenyl, optionally substituted, comprising 5-14, e.g. 8, 9, 10 or 11, carbon atoms (e.g. 2,6,6-trimethylcyclohex-1-enyl, 2,6,6-trimethylcyclohex-2-enyl, 2,6,6-trimethylcyclohex-3-enyl, 6,6-dimethyl-2-methylenecyclohexyl, 2,6,6-trimethylcyclohex-1,3-dien-1-yl, 2-ethyl-6-methylcyclohex-2-en-1-yl, 2-ethyl-3,6,6-trimethylcyclohex-4-en-1-yl, 2,4,4-trimethylcyclohex-2-en-1-yl, and 2-ethyl-5,5-dimethylcyclopent-2-en-1-yl), and spirobicycloalkyl and spirobicycloalkenyl, optionally substituted, comprising 8-13 carbon atoms (e.g. 7-methylspiro[4.5]dec-6-ene-6-yl, 7-methylspiro[4.5]dec-7-ene-6-yl, 7-methylspiro[4.5]dec-8-ene-6-yl, 7-methylenespiro[4.5]dec-6-yl);

R³ and R⁴ are independently selected from the group consisting of hydrogen, phenyl, linear and branched $C_1$-$C_6$ alkyl and alkenyl (e.g. methyl, ethyl, isopropyl, hexyl), cycloalkenyl, optionally substituted, comprising 5-12 carbon atoms (e.g. cyclohex-3-en-1-yl), and cycloalkenylalkyl, optionally substituted, comprising 6-14 carbon atoms (e.g. (2,2,3-trimethylcyclopent-3-enyl)methyl);

R⁶ and R⁷ are independently selected from hydrogen, linear and branched $C_1$-$C_6$ alkyl and alkenyl (e.g. propyl, methyl, ethyl, hexyl, isopropyl, hexenyl), and cycloalkyl, optionally substituted, comprising 3-14 carbon atoms (e.g. 3,3-dimethylcyclohex-1-enyl, cyclohexyl); or at least one of the pairs R¹ and R⁷, R² and R⁶, R³ and R⁷, R⁴ and R⁶ forming together with the carbon atoms to which they are attached a mono- or bicyclic ring system comprising 5 to 10 carbon atoms (e.g. e.g. spiro[4.5]decane, 3,3-dimethylcyclohexane, 5,5-dimethylcyclohexane, cyclopentane, cyclohexane, cyclooctane, cycloheptane, cyclohexanone, cyclopentanone); and R⁵ is selected from the group consisting of linear and branched $C_1$-$C_5$ alkyl (e.g. methyl, ethyl, propyl, isopropyl, butyl), and $C_7$-$C_{10}$ arylalkyl (e.g. benzyl), optionally substituted with 1, 2, or 3 hetero atoms selected from N, S and O;

comprising admixing a 2-amino-3-mercapto propionic acid ester of formula (II) or a salt thereof

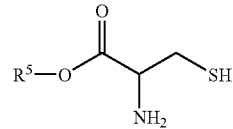

(II)

wherein R⁵ has the same meaning as given above;

with 2 equivalents of a substituted 3-buten-2-one of formula (IIIa and IIIb), optionally in the presence of a base, such as $K_2CO_3$ or ethyl diisopropyl amine

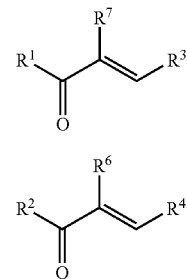

IIIa

IIIb wherein R¹ to R⁴, R⁶ and R⁷ have the same meaning as given above.

Non limiting examples are those compounds of formula (IIIa)/(IIIb) selected from the group consisting of 3-methyl-5-(2,2,3-trimethylcyclopent-3-enyl)pent-3-en-2-one; 1-(spiro[4.5]dec-7-en-7-yl)pent-4-en-1-one; 1-(2,6,6-trimethylcyclohexa-1,3-dienyl)but-2-en-1-one; 2,7-dimethyloct-5-en-4-one; 1-(6-ethyl-2-methylcyclohex-3-enyl)but-2-en-1-one; 1-(2-ethyl-3,6-dimethylcyclohex-2-enyl)but-2-en-1-one; 1-(2,4,4-trimethylcyclohex-2-enyl)but-2-en-1-one; 5-methylhept-2-en-4-one; 1-(2-ethyl-5,5-dimethylcyclopent-2-enyl)but-2-en-1-one; 5,6,7-trimethylocta-2,5-dien-4-one; 1-(5,5-dimethylcyclohex-1-enyl)pent-4-en-1-one; 1-(5,5-dimethylcyclohex-1-enyl)pent-4-en-1-one; 1-(2,6,6-trimethylcyclohex-2-enyl)but-2-en-1-one; 1-(2,6,6-trimethylcyclohex-1-enyl)but-2-en-1-one; 1-(2,6,6-trimethylcyclohex-3-enyl)but-2-en-1-one; 1-(7-methylspiro[4.5]dec-8-en-6-yl)but-2-en-1-one; 1-(7-methylspiro[4.5]dec-7-en-6-yl)but-2-en-1-one; 1-(7-methylspiro[4.5]dec-6-en-6-yl)but-2-en-1-one; and 1-(7-methylenespiro[4.5]decan-6-yl)but-2-en-1-one.

The invention is now further described with reference to the following non-limiting examples. These examples are for the purpose of illustration only and it is understood that variations and modifications can be made by one skilled in the art without departing from the scope of the invention. It should be understood that the embodiments described are not only in the alternative, but can be combined.

EXAMPLE 1

Methyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate (Compound 1)

A solution of 1-(2,6,6-trimethylcyclohex-3-enyl)but-2-en-1-one (19.28 g, 100 mmol, 2 equiv.), ethyl diisopropylamine (6.45 g, 50 mmol, 1 equiv.) and L-Cystein methyl ester hydro-

9 chloride (8.60 g, 50 mmol, 1 equiv.) in MeOH (120 ml) is heated to reflux during 28 h. The solvent is removed in vacuo and the residue dissolved in methyl t-butyl ether. The solution is washed with dilute aq. NaCl, dried over $MgSO_4$ and concentrated. The residue is purified by chromatography on $SiO_2$ to yield 21.3 g (82%) of the title compound as yellowish, viscous oil.

$^1$H-NMR ($CDCl_3$, 400 MHz): 5.49-5.42 (m, 2H), 5.40-5.34 (m, 2H), 3.69-3.66 (series of s, 3H), 3.52-3.43 (m, 1H), 3.30-3.22 (m, 1H), 3.13-3.04 (m, 1H), 2.87-2.27 (series of m, 8H), 2.19-2.10 (m, 2H), 1.96 (br. s, 1H), 1.89, 1.62 (AB, $J_{AB}$=17 Hz, 4H), 1.26-1.15 (m, 3H), 1.05-0.96 (m, 3H), 0.94-0.76 (m, 18H).

$^{13}$C-NMR ($CDCl_3$, 100 MHz): 213.7 (s), 213.6 (s), 213.4 (2s), 211.9 (3s), 211.8 (3s), 174.4 (4s), 173.9 (3 s), 173.8 (s), 131.7 (4 d), 131.6 (d), 124.1 (d), 124.0 (3 d), 123.9 (d), 63.0 (d), 62.9 (3 d), 62.8 (2 d), 62.7 (2 d), 59.6 (d), 59.5 (d), 59.4 (d), 59.3 (d), 58.8 (d), 58.7 (3 d), 58.6 (d), 55.3 (t), 55.2 (2 t), 55.0 (3 t), 54.9 (3 t), 54.8 (2 t), 51.9 (3 q), 51.8 (2 q), 47.7 (2 d), 47.6 (3 d), 47.5 (d), 47.0 (d), 46.9 (3 d), 46.8 (d), 41.6 (3 t), 34.8 (d), 34.7 (d), 34.6 (3 d), 34.5 (2 d), 34.3 (2 t), 34.2 (2 t), 34.1 (2 t), 34.0 (t), 33.0 (2 s), 32.9 (3 s), 31.6 (2 d), 31.5 (2 d), 31.4 (3 d), 29.7 (q), 29.6 (q), 21.7 (2 q), 21.6 (3 q), 21.5 (2 q), 21.4 (2 q), 21.2 (2 q), 20.6 (3 q), 20.0 (q), 19.9 (3 q), 19.8 (3 q), 19.7 (q).

IR (film): 2956 m, 1736 s, 1704 vs, 1456 m, 1367 s, 155 s, 683 s.

MS (EI): 519 (15, M$^+$), 460 (32), 194 (5), 368 (5), 309 (11), 295 (25), 280 (85), 268 (9), 208 (13), 123 (57), 116 (31).

EXAMPLE 2

Methyl 2-(5,6,7-trimethyl-4-oxooct-5-en-2-ylamino)-3-(5,6,7-trimethyl-4-oxooct-5-en-2-ylthio)propanoate (Compound 2)

A solution of 5,6,7-trimethylocta-2,5-dien-4-one (16.64 g, 100 mmol, 2 equiv.), ethyl diisopropylamine (6.45 g, 50 mmol, 1 equiv.) and L-Cystein methyl ester hydrochloride (8.61 g, 50 mmol, 1 equiv.) in MeOH is heated to reflux for 18 h. The solvent is removed in vacuo and the residue purified by chromatography on $SiO_2$ to yield 11.0 g (50%) of the title compound as yellow oil. The product consists of a mixture of diastereomers.

$^1$H-NMR ($CDCl_3$, 400 MHz): 3.70 (3s, 3H), 3.54-3.46 (m, 1H), 3.32-3.25 (m, 1H), 3.15-3.09 (m, 1H), 2.79-2.68 (m, 5H), 2.61-2.40 (m, 3H), 1.93 (br. s, 1H), 1.77-1.75, 1.71-1.70 (2 m, 6H), 1.60-1.59, 1.54-1.53 (2 m, 6H), 1.25-1.19 (m, 3H), 1.05-1.02 (m, 3H), 0.94-0.90 (series of d, 12H).

$^{13}$C-NMR (100 MHz): 211.2, 208.0, 207.8, 206.4 (s), 174.4, 173.9 (s), 143.4, 143.0, 142.9, 142.8 (s), 130.9, 130.8, 130.5, 130.0 (s), 59.4, 59.3, 58.8, 58.7 (d), 52.0, 51.9 (q), 49.6, 49.4, 49.3, 49.1 (t), 48.7, 48.6 (d), 47.8, 47.7 (d), 35.8, 35.7, 35.6 (d), 34.2 (2 d), 31.7 (d), 30.1 (d), 21.5, 21.2 (q), 20.8 (q), 20.1, 19.9 (q), 15.1 (2 q), 14.3, 14.2 (q), 13.8 (q), 12.1 (2 q).

IR (film): 2960 s, 2870 m, 1738 vs, 1682 vs, 1163 s, 1018 m.

MS (EI): 467 (13, M$^+$), 424 (13), 408 (18), 342 (10), 268 (24), 254 (100), 212 (26), 167 (23), 166 (26), 125 (52), 114 (52).

EXAMPLE 3

Ethyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate (Compound 3)

A solution of 1-(2,6,6-trimethylcyclohex-3-enyl)but-2-en-1-one (83.0 g, 0.50 mol, 2 equiv.), ethyl diisopropylamine (32.3 g, 0.25 mol, 1 equiv.) and L-Cystein ethyl ester hydrochloride (46.5 g, 0.25 mol, 1 equiv.) in EtOH (600 ml) is heated to 60° C. during 44 h. The solvent is removed in vacuo and the residue dissolved in methyl t-butyl ether. The solution is washed with dilute aq. NaCl, dried over $MgSO_4$ and concentrated. The residue is purified by chromatography on $SiO_2$ to yield 85.5 g (71%) of the title compound as orange oil.

$^1$H-NMR ($CDCl_3$, 400 MHz): 5.50-5.43 (m, 2H), 5.40-5.35 (m, 2H), 4.22-4.11 (m, 2H), 3.51-3.40 (m, 1H), 3.33-3.23 (m, 1H), 3.15-3.05 (m, 1H), 2.88-2.28 (series of m, 8H), 2.19-2.11 (m, 2H), 1.97 (br. s, 1H), 1.92 (br. s, 1H), 1.87 (br. s, 1H), 1.64 (br. s, 1H), 1.60 (br. s, 1H), 1.25-1.21 (m, 6H), 1.05-1.00 (m, 3H), 0.94-0.80 (m, 18H).

$^{13}$C-NMR ($CDCl_3$, 100 MHz): 213.4 (2 s), 211.9 (3 s), 173.9 (2 s), 173.4 (3 s), 131.7 (3 d), 131.6 (d), 124.1 (3 d), 124.0 (2 d), 63.0 (2 d), 62.9 (2 d), 62.8 (3 d), 62.7 (2 d), 60.9 (3 t), 60.8 (2 t), 59.5 (d), 59.3 (2 d), 58.8 (d), 58.7 (2 d), 55.3 (3 t), 55.1 (2 t), 55.0 (3 t), 54.9 (2 t), 54.8 (t), 47.7 (2 d), 47.6 (2 d), 46.9 (2 d), 46.8 (d), 41.6 (2 t), 34.8 (2 d), 34.7 (d), 34.6 (3 d), 34.4 (t), 34.3 (t), 34.2 (t), 34.1 (t), 31.7 (d), 31.6 (2 d), 31.5 (3 d), 31.4 (3 d), 29.7 (2 q), 21.7 (q), 21.6 (2 q), 21.5 (2 q), 21.4 (2 q), 21.3 (q), 21.1 (q), 20.6 (2 q), 20.1 (2 q), 20.0 (q), 19.9 (3 q), 19.8 (4 q).

IR (film): 3018 w, 2958 m, 1733 s, 1704 vs, 1458 m, 1367 s, 1178 m, 1155 m, 683 m.

MS (EI): 533 (11, M$^+$), 460 (19), 309 (11), 295 (17), 294 (100), 130 (74), 123 (28).

EXAMPLE 4

Ethyl 2-(5,6,7-trimethyl-4-oxooct-5-en-2-ylamino)-3-(5,6,7-trimethyl-4-oxooct-5-en-2-ylthio)propanoate (Compound 4)

A solution of 1-(2,6,6-trimethylcyclohex-3-enyl)but-2-en-1-one (96.0 g, 0.50 mol, 2 equiv.), ethyl diisopropylamine (32.3 g, 0.25 mol, 1 equiv.) and L-Cystein ethyl ester hydrochloride (46.5 g, 0.25 mol, 1 equiv.) in EtOH (600 ml) is heated to 65° C. during 4 days. The solvent is removed in vacuo and the residue dissolved in methyl t-butyl ether. The solution is washed with dilute aq. NaCl, dried over $MgSO_4$ and concentrated. The residue is purified by chromatography on $SiO_2$ to yield 84 g (63%) of the title compound as yellowish, viscous oil.

$^1$H-NMR ($CDCl_3$, 400 MHz): 4.20-4.12 (m, 2H), 3.51-3.42 (m, 1H), 3.34-3.26 (m, 1H), 3.16-3.09 (m, 1H), 2.81-2.39 (series of m, 8H), 1.96 (br. s, 1H), 1.86 (dd, J=6.8, 1.5 Hz, 0.5H), 1.77-1.73 (m, 2H), 1.71-1.68 (m, 5H), 1.65-1.62 (m, 0.5H), 1.60-1.58 (2 m, 1H), 1.56-1.51 (m, 5H), 1.27-1.20 (m, 5H), 1.06-1.01 (m, 3H), 0.95-0.86 (m, 9H).

$^{13}$C-NMR ($CDCl_3$, 100 MHz): 208.0 (s), 207.7 (2 s), 206.4 (2 s), 206.3 (s), 173.9 (s), 173.4 (s), 143.4 (2 s), 142.9 (s), 142.8 (2 s), 130.8 (s), 130.5 (2 s), 61.0 (t), 60.9 (t), 59.5 (d), 59.4 (d), 58.8 (d), 58.7 (d), 49.7 (t), 49.4 (t), 49.3 (t), 49.1 (t), 48.7 (d), 48.6 (d), 47.8 (d), 47.7 (d), 35.7 (2 d), 35.6 (2 d), 34.3 (2 t), 34.2 (t), 31.7 (3 d), 30.1 (d), 21.5 (2 q), 21.2 (q), 20.8 (q), 20.5 (q), 20.1 (q), 19.9 (q), 19.8 (q), 15.1 (2 q), 14.3 (q), 14.2 (q), 14.1 (q), 13.8 (q), 12.1 (2 q).

IR (film): 2962 s, 1734 vs, 1682 vs, 1463 m, 180 vs, 1161 vs, 1025 s.

MS (EI): 481 (7, M+), 438 (6), 408 (19), 356 (7), 82 (10), 269 (15), 268 (100), 26 (18), 167 (21), 16 (19), 151 (13), 130 (14), 128 (38), 125 (41), 102 (29).

EXAMPLE 5

Soap Bar

Compound 3 (see Example 3) and compound 4 (see Example 4), i.e. a malodor counteractant (MOC) according to formula (I), was added at a dosage of 0.001% and 0.005% by weight, respectively, to a soap base, judged to have malodor, as hereinunder described. The base was milled thoroughly and soap bars were made. Soap bars without the MOC-ingredient were made as a control. The bars were allowed to macerate at 40° C. overnight and the headspace concentration of the volatile components of the experimental bar and the control soap bar was determined by placing the bar in a suitable container and drawing an appropriate amount of the headspace through a Tenax trap. The headspace samples were analyzed by thermally desorbing the volatile components from the trap into an Agilent 6890 capillary GC fitted with a high sensitivity mass selective detector. The components were identified using a proprietary in-house mass spectral database and quantified. The following malodor components have been identified: hexanal, heptanal, hexanoic acid, methyl hexyl ketone, methyl nonyl ketone, octanal, octanoic acid, pentanal, and valeric acid.

In addition the mixtures were evaluated by 5 organoleptically trained experts using the following 5 point scale: 1=No malodor, 2=Slight malodor, 3=moderate malodor, 4=slightly strong malodor, 5=strong malodor.

All results are shown in Table 1a and 1b, below.

TABLE 1a

Malodor concentration/intensity of soap base.

| | Concentration of malodor components (ng/l) | Malodor intensity rating |
|---|---|---|
| Control Base | 549.3 | 5.0 |
| Base containing 0.001% compound 4 | 209.6 | 1.8 |
| Base containing 0.005% compound 4 | 113.4 | 1.0 |

TABLE 1b

Malodor concentration/intensity of soap base.

| | Concentration of malodor components (ng/l) | Malodor intensity rating |
|---|---|---|
| Control Base | 562.7 | 5.0 |
| Base containing 0.001% compound 3 | 247.3 | 2.0 |
| Base containing 0.005% compound 3 | 128.5 | 1.0 |

The presence of a compound of formula (I) significantly reduces the malodor components and the malodor intensity.

The compounds, alone or mixtures thereof may be used in similar solid or liquid soap bases to reduce the malodor.

EXAMPLE 6

Fabric Washing Detergent 0.05% of compound 3 (see Example 3) and compound 4 (see Example 4) respectively was added to a concentrated fabric washing detergent base judged to have a strong base odor. The concentrated fabric washing detergent base was used as the control. The bases were left to macerate at 40° C. overnight. The malodor ingredients in the headspace of the base were determined by collecting sufficient samples of the respective headspace of the macerated bases and analyzing as per the method outlined in Example 5. The following malodor components have been identified: dodecanal, methyl ethyl ketone, methyl hexyl ketone, trimethyl amine, and octanal.

In addition these bases were evaluated by 5 organoleptically trained experts using the scale outlined in Example 5.

All results are shown below in Table 2a and 2b.

TABLE 2a

Malodor concentration/intensity of fabric washing detergent base

| | Concentration of malodor components (ng/l) | Malodor intensity rating |
|---|---|---|
| Control Base | 161.2 | 5.0 |
| Base containing 0.05% compound 4 | 31.8 | 1.2 |

TABLE 2b

Malodor concentration/intensity of fabric washing detergent base

| | Concentration of malodor components (ng/l) | Malodor intensity rating |
|---|---|---|
| Control Base | 155.4 | 5.0 |
| Base containing 0.05% compound 3 | 35.7 | 1.2 |

Compounds of formula (I) significantly reduces the malodor components and the malodor intensity. The results indicate that the compounds of formula (I) can be used in a wide range of substrate washing products to markedly improve the base odor.

EXAMPLE 7

Fabric Softener 0.1% of compound 3 (see Example 3) and compound 4 (see Example 4) respectively, was added to concentrated fabric softener base considered to have a strong base malodor. The concentrated fabric softener base was used as the control. The bases were left to macerate at 40° C. overnight. The headspace of the concentrated fabric softener were collected and analyzed as per Example 5. The following malodor components have been identified: heptanal, hexanal, methyl pentyl ketone, nonanal, octanal, pentanal, and 2-pentyl furan.

In addition the bases were evaluated by 5 organoleptically trained experts as per Example 5.

All results are shown in Table 3a and 3b below.

TABLE 3a

Malodor concentration/intensity of concentrated fabric softener product.

| | Concentration of malodor components (ng/l) | Malodor intensity rating |
|---|---|---|
| Control Base | 1918.2 | 5.0 |
| Base containing compound 4 | 442.1 | 1.0 |

TABLE 3b

Malodor concentration/intensity of concentrated fabric softener product.

| | Concentration of malodor components (ng/l) | Malodor intensity rating |
|---|---|---|
| Control Base | 1433.4 | 5.0 |
| Base containing compound 3 | 494.3 | 1.0 |

Compounds of formula (I) significantly reduces the malodor components/malodor intensity. The results indicate that the compounds of the present invention can be used in a wide range of substrate conditioning products to markedly improve the base odor.

EXAMPLE 8

Fabric Softener

Terry toweling test pieces were rinsed in the concentrated fabric softener product as described in Example 7, in a Terg-O-Tometer using tap water at 25° C. with a cloth to liquor ratio of 1:25, a product concentration of 0.2% and an agitation of 65 rpm for 5 min. The test pieces were spun dry to a constant weight. The test pieces were then line dried. Each test piece was placed in a glass headspace collection vessel and the headspace an analysis was carried out as per Example 5. The total amount of malodor components (i.e. heptanal, hexanal, methyl pentyl ketone, nonanal, octanal, pentanal, and 2-pentyl furan) determined in the headspace is shown below in Table 4a and 4b.

TABLE 4a

The concentration of malodor components in headspace of treated towels.

| | Concentration of malodor components (ng/l) |
|---|---|
| Control Base | 54.7 |
| Base containing compound 4 | 19.2 |

TABLE 4b

The concentration of malodor components in headspace of treated towels.

| | Concentration of malodor components (ng/l) |
|---|---|
| Control Base | 89.3 |
| Base containing compound 3 | 23.7 |

The malodorous base transferred the malodor ingredients to the treated cloth. The compounds of formula (I) significantly reduced the malodor components on the toweling. A benefit is clearly imparted with respect to reducing the malodor of substrates treated with a consumer product base that contains malodor moieties.

EXAMPLE 9

Fragrance Compositions

| Ingredient | % (w/w) |
|---|---|
| Benzyl Alcohol | 5.00 |
| Cinnamyl Alcohol | 5.00 |
| Dihydromyrcenol | 6.00 |
| Diphenyl Oxide | 2.50 |
| Heliotropin | 1.00 |
| Citronellyl Acetate | 5.00 |
| Indole | 0.10 |
| Hedione | 10.00 |
| Phenyl Ethyl Alcohol | 5.75 |
| Myrascone | 2.50 |
| Linalyl Butyrate | 5.00 |
| Mayol | 10.50 |
| Terpineol | 16.60 |
| Vanillin | 0.05 |

Composition 1: fragrance composition according to the formula above plus 25% (w/w) of diethyl phthalate, a low odor solvent.

Composition 2: fragrance composition according to the formula above plus 15% (w/w) of diethyl phthalate and 10% (w/w) ethyl 2-(5,6,7-trimethyl-4-oxooct-5-en-2-ylamino)-3-(5,6,7-trimethyl-4-oxooct-5-en-2-ylthio)propanoate (compound 4).

Composition 3: fragrance composition according to the formula above plus 15% (w/w) of diethyl phthalate and 10% (w/w) ethyl 2-(4-oxo-4-(2,6,6-trimethylcyclohex-3-enyl)butan-2-ylamino)-3-(4-oxo-4-(2,6,6-trimethylcyclohex-3-enyl)butan-2-ylthio)propanoate (compound 3).

Each composition was placed at 0.3% into a concentrated fabric washing detergent base. The base was left to macerate at 40° C. overnight. A group of 10 organoleptically trained people have been asked to compare composition 1 with 2 and composition 1 with 3 respectively, and indicate the most preferred one. 90% of the panelists selected composition 2 and all panelists selected composition 3.

Compounds of formula (I) when incorporated into a base enhance the perception of the fragrance as less fragrance is used to mitigate the malodor of the base. The compounds of the present invention may be used either to maximize fragrance pleasantness or allow the reduction of the level of fragrance maintaining the pleasantness of the end-product.

The invention claimed is:

1. A method of producing a compound of formula (I)

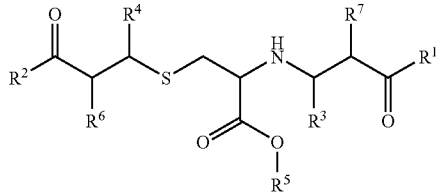

wherein
- $R^1$ and $R^2$ are independently selected from the group consisting of linear and branched $C_1$-$C_{14}$ alkyl and alkenyl, cycloalkyl and cycloalkenyl, optionally substituted, comprising 5-14 carbon atoms, and spirobicycloalkyl and spirobicycloalkenyl, optionally substituted, comprising 8-13 carbon atoms;
- $R^3$ and $R^4$ are independently selected from the group consisting of hydrogen, phenyl, linear and branched $C_1$-$C_6$ alkyl and alkenyl, cycloalkenyl, optionally substituted, comprising 5-12 carbon atoms, and cycloalkenylalkyl, optionally substituted, comprising 6-14 carbon atoms;
- $R^6$ and $R^7$ are independently selected from hydrogen, linear and branched $C_1$-$C_6$ alkyl and alkenyl, and cycloalkyl, optionally substituted, comprising 3-14 carbon atoms; or
- at least one of the pairs $R^1$ and $R^7$, $R^2$ and $R^6$, $R^3$ and $R^7$, $R^4$ and $R^6$ forming together with the carbon atoms to which they are attached a mono- or bicyclic ring system comprising 5 to 10 carbon atoms; and
- $R^5$ is selected from the group consisting of linear and branched $C_1$-$C_5$ alkyl, and $C_7$-$C_{10}$ aralkyl, optionally substituted with 1, 2 or 3 hetero atoms selected from N, S and O;

the method comprising the step of: admixing an 2-amino-3-mercapto propionic acid ester of formula (II) or a salt thereof

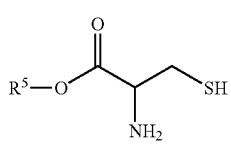

wherein $R^5$ has the same meaning as given above;
with at least 2 equivalents of a substituted 3-buten-2-one of formula (IIIa and IIIb)

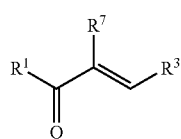

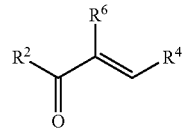

wherein $R^1$ to $R^4$, $R^6$ and $R^7$ have the same meaning as given above.

2. A method according to claim 1 wherein a base is added to the admixture.

3. A method according to claim 2 wherein the base is selected from $K_2CO_3$ and ethyl diisopropyl amine.

4. A compound of formula (I)

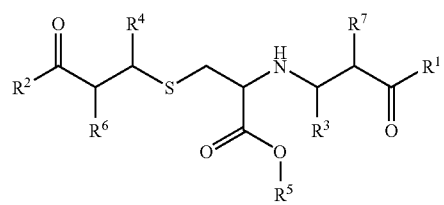

wherein
- $R^1$ and $R^2$ are independently selected from the group consisting of linear and branched $C_1$-$C_{14}$ alkyl and alkenyl, cycloalkyl and cycloalkenyl, optionally substituted, comprising 5-14 carbon atoms, and spirobicycloalkyl and spirobicycloalkenyl, optionally substituted, comprising 8-13 carbon atoms;
- $R^3$ and $R^4$ are independently selected from the group consisting of hydrogen, phenyl, linear and branched $C_1$-$C_6$ alkyl and alkenyl, cycloalkenyl, optionally substituted, comprising 5-12 carbon atoms, and cycloalkenylalkyl, optionally substituted, comprising 6-14 carbon atoms;
- $R^6$ and $R^7$ are independently selected from hydrogen, linear and branched $C_1$-$C_6$ alkyl and alkenyl, and cycloalkyl, optionally substituted, comprising 3-14 carbon atoms; or
- at least one of the pairs $R^1$ and $R^7$, $R^2$ and $R^6$, $R^3$ and $R^7$, $R^4$ and $R^6$ forming together with the carbon atoms to which they are attached a mono- or bicyclic ring system comprising 5 to 10 carbon atoms; and
- $R^5$ is selected from the group consisting of linear and branched $C_1$-$C_5$ alkyl, and $C_7$-$C_{10}$ aralkyl, optionally substituted with 1, 2 or 3 hetero atoms selected from N, S and O.

5. A compound according to claim 4 wherein $R^1$=$R^2$, $R^3$=$R^4$ and $R^6$=$R^7$.

6. A compound according to claim 4 wherein $R^5$ is methyl or ethyl.

7. A method of reducing malodor the method comprising the step of: admixing to a consumer product a compound of formula (I) according to claim 1.

8. A consumer product comprising a compound of formula (I) according to claim 1, and a consumer product base.

* * * * *